(12) United States Patent
Pascaly et al.

(10) Patent No.: US 7,393,972 B2
(45) Date of Patent: Jul. 1, 2008

(54) PROCESS FOR PREPARING AMINO ACID ESTERS AND THEIR ACID ADDITION SALTS

(75) Inventors: Matthias Pascaly, Münster (DE); Dietrich Maaβ, Altenberge (DE); Dieter Buβ, Aschaffenburg (DE); Burghard Grüning, Essen (DE); Gunter Latoschinski, Marl (DE); Tim Pöpken, Friesoythe (DE); Christian Weitemeyer, Essen (DE)

(73) Assignee: Goldschmidt GmbH, Essen (DE)

( * ) Notice: Subject to any disclaimer, the term of this patent is extended or adjusted under 35 U.S.C. 154(b) by 590 days.

(21) Appl. No.: 11/061,420

(22) Filed: Feb. 18, 2005

(65) Prior Publication Data

US 2005/0192460 A1 Sep. 1, 2005

(30) Foreign Application Priority Data

Feb. 19, 2004 (DE) .................. 10 2004 008 042

(51) Int. Cl.
*C07C 67/00* (2006.01)
(52) U.S. Cl. .................. 560/204; 560/155; 554/161
(58) Field of Classification Search ............... 560/204, 560/155, 156; 554/161
See application file for complete search history.

(56) References Cited

OTHER PUBLICATIONS

Angier et al, Journal of Organic Chemistry, 21, 1540-1543, 1956.*
1) Becker et al, *Organikum*, "Reactions of Carbonyl Compounds", pp. 474-480, Germany.
2) G.C. Barrett, *Amino Acid Derivatives A Practical Approach*, "Reactions at the Carboxy Group of an Amino Acid—Esterification of Amino Acids", pp. 38-49.
3) Emil Fischer, *Bertichte Der Deutschen Chemischen Gesellschaft*, "Synthese von Polypeptiden", pp. 2893-2931 (1906).
4) M. Brenner, et al, *Helvetica Chimica Acta*, "Herstellung von Alpha-Aminosaureestern durch Alkohlyse der Methylester", vol. XXXVI, No. 136-137, pp. 1109-1115, (1953); and.
5) M. Dymicky et al, *Analytical Biochemistry, An International Journal*, "A General, Highly Efficient Azeotropic Method of Esterification of Amino Acids", vol. 41, No. 1, pp. 487-491 (1971).

* cited by examiner

*Primary Examiner*—Shailendra Kumar
(74) *Attorney, Agent, or Firm*—Scully, Scott, Murphy & Presser, P.C.

(57) ABSTRACT

The invention provides a process for preparing amino acid esters and/or their acid addition salts from monomeric or polymeric amino acids, peptides, proteins and alcohols, which comprises carrying out the reaction in supercritical alcohols, preferably at pressures and temperatures which are at least 5% above the critical parameters, the alcohols serving both as the solvent and as reactants.

15 Claims, 1 Drawing Sheet

PROCESS FOR PREPARING AMINO ACID ESTERS AND THEIR ACID ADDITION SALTS

FIELD OF THE INVENTION

The present invention provides a process for synthesizing amino acid esters and their acid addition salts using a simple and inexpensive technique. The inventive process prepares the aforementioned products in high space-time yields, continuously or batchwise, by direct reaction of polypeptides, proteins or amino acids, substantially without the additions of a catalyst or an activator.

BACKGROUND OF THE INVENTION

In contrast to the synthesis of carboxylic esters, which generally proceeds without any problem by a proton-catalyzed reaction of the free acid with an alcohol, typically with the additional use of acidic catalysts, for example sulfuric acid, hydrogen chloride gas, toluenesulonic acid or acidic ion exchangers (see, for example, Organikum, 21st edition, p. 474 ff), an esterification of a carboxylic acid group of amino acids is only possible with difficulty and with addition of the abovementioned activators or catalysts. Additionally, the esterification of the carboxylic acid group of amino acids using such a technique typically results in moderate yields (from 45 to 90%, depending on the amino acid). See, for example, G. C. Barrett, Amino Acid Derivatives (1999), 37.

The solubilities of amino acids are determined by the typical zwitterionic structure. In the solid state and in solution, a carboxylate and an ammonium group are present As a result, amino acids dissolve readily only in water, but only very slowly and with difficulty in alcohol, if at all. This considerably prolongs the reaction time in comparison to alkylcarboxylic acids.

For an esterification, the solid is initially suspended in an alcohol. Subsequently, hydrogen chloride can be passed through the mixture. See, for example, E. Fischer, Ber. Dt Chem. Ges. 39 (1906), 2893. An alternative approach is the stoichiometric addition of thionyl chloride. See, for example, M. Brenner, W. Huber, Helv. Chim. Acta 36 (1953), 1109.

In order to further increase the reaction rate, the mixture may be heated. After a few hours (or even days), the products are obtained as hydrochlorides.

It is also known that the process of azeotropic distillation can be used for the preparation of amino acid esters. This is reported, for example, in M. Dymicky, E. F. Mellon, J. Naghski, Anal. Biochem. 41 (1971), 487.

However, all of these preparation processes are time-consuming batch syntheses of the corresponding amino acid esters which can decompose as a result of reactions of the amino acid side chains under the reaction conditions required.

One method of preparing amino acid esters directly from proteins or peptides is possible according to the prior art only in a laborious process by hydrolytic cleavage (enzymatically with proteases or peptidases or chemically by acid catalysis) in a first step and subsequent esterification of the fragments. When the abovementioned prior art method is used, a multitude of by-products and a high salt burden are obtained.

There is therefore still a need for a method for the simple and inexpensive synthesis of amino acid esters and their acid addition salts, in which these products can be prepared in high space-time yields, continuously or batchwise, by direct reaction of peptides, proteins or amino acids, substantially without additions of catalysts or activators.

SUMMARY OF THE INVENTION

The present invention provides a process for synthesizing amino acid esters and their acid addition salts using a simple and inexpensive technique. The inventive process prepares the aforementioned products in high space-time yields, continuously or batchwise, by direct reaction of polypeptides, proteins or amino acids, substantially without the additions of a catalyst or an activator.

It has now been found that, surprisingly, proteinogenic and nonproteinogenic amino acids, and also peptides and proteins, can be reacted in alcohols at high pressures and high temperatures, in the course of which both parameters have to attain at least the critical values of the alcohol, by reaction of the acid component with the alcohol. The inventive process thus provides a simple esterification reaction It has also been found that peptides can be cleaved under these conditions into their basic building blocks, the amino acids, to form esterified monomers. This is shown for example, in Scheme 1 provided herein below.

The present invention provides a process for preparing amino acid esters and/or acid addition salts thereof from monomeric or polymeric ammo acids, peptides, proteins and alcohols, which comprises carrying out the reaction in supercritical alcohols, preferably at pressures and temperatures which are ≧5% above the critical parameters.

BRIEF DESCRIPTION OF THE DRAWINGS

The sole FIGURE, FIG. 1, provides a schematic illustration of the apparatus that can be used in the present invention. In the drawing, A is the vessel, B and B$^1$ are pumps, C is the reactor, D is a heater, E is a valve, F is the carrier stream reservoir, G is carrier stream preheater and H is the mixing point.

DETAILED DESCRIPTION OF THE INVENTION

Figure 1:
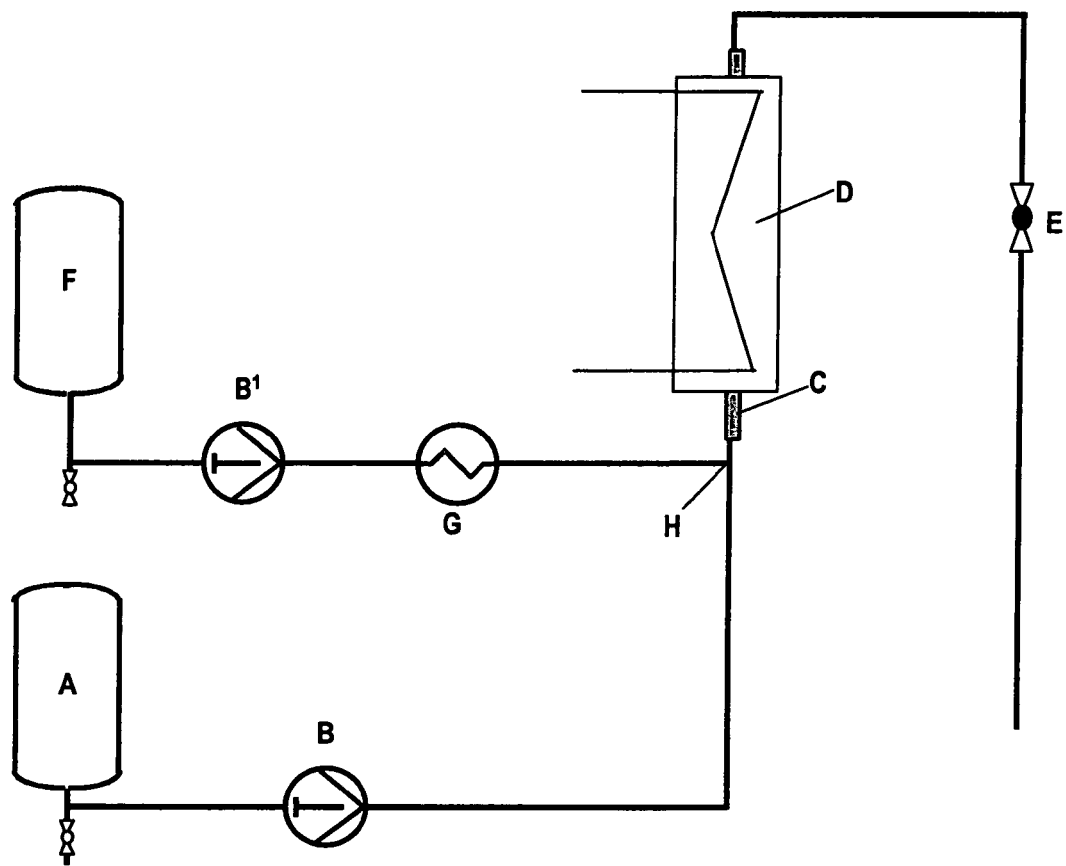

The present invention, which provides a process for synthesizing amino acid esters and their acid addition salts using a simple and inexpensive technique, in which the products are produced in high space-time yields, continuously or batchwise, by direct reaction of polypeptides, proteins or amino acids, substantially without the additions of a catalyst or an activator, will now be described in greater detail.

As stated above it has now been surprisingly found that proteinogenic and nonproteinogenic amino acids, and also peptides and proteins, can be reacted in alcohols at high pressures and high temperatures, m the course of which both parameters have to attain at least the critical values of the alcohol, by reaction of the acid component with the alcohol. Also, and as stated above, it has also been found that peptides can be cleaved under these conditions into their basic building blocks, the amino acids, to form esterified monomers.

Specifically, in the inventive conversion of monomeric or polymeric amino acids, peptides or proteins, reaction in supercritical alcohols affords the amino acid esters according to the general scheme 1:

Scheme 1: Reaction of a polymeric amino acid with alcohol

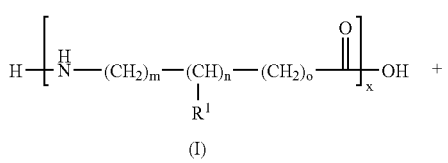

(I)

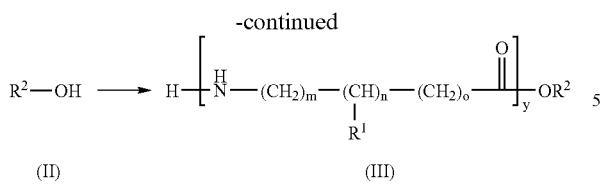

In the amino acids, peptides, proteins and polyamides of the general formula (I) which can be used in accordance with the present invention:

$R^1$ is at least one radical selected from the group of H, linear or branched aliphatic, alicyclic, heterocyclic, saturated, unsaturated or aromatic radical or proteinogenic or nonproteinogenic amino acids, n is at least 1, preferably from 1 to 11, in particular 1, 2, 3, 5 or 11, m,o are each independently from 0 to 20, preferably from 0 to 12, x is $\geq 1$, and y is $\leq x$, preferably from 1 to 10.

Compounds of the formula I suitable for the process according to the present invention include, for example, proteinogenic and nonproteinogenic amino acids, in particular, glycine, lysine, aspartic acid, asparagine, alanine, proline, valine, glutamic acid, glutamine, leucine, isoleucine, serine, phenylalanine, tyrosine, histidine, threonine, cysteine, methionine, tryptophan, tert-leucine, β-alanine, γ-aminobutyric acid, ω-aminocaproic acid, phenylglycine, arginine and amino acid derivatives, in particular, pyrrolidinecarboxylic acid, pyrrolidone, ε-caprolactam, and also low and high molecular weight proteins, in particular, casein, keratin, soya, collagen, wheat proteins, almond proteins, silk proteins, hydrolyzates thereof, and also poly(6-aminocaproic acid) and poly(12-aminododecanoic acid).

Suitable as reactants and simultaneously solvents are in principle all alcohols. In the alcohols of the general formula (II) which can be used in accordance with the invention:

$R^2$ is an optionally branched hydrocarbon radical, optionally containing double bonds, hydroxyalkyl, alkyloxy, having from 1 to 30 carbon atoms, preferably from 1 to 18, where the radical may also have alicyclic or heterocyclic components, saturated, unsaturated or aromatic, having a ring size from 3 to 10 atoms, preferably from 4 to 6 atoms, which may bear further, saturated or unsaturated hydrocarbon substituents having from 1 to 30 carbon atoms, preferably from 1 to 18 carbon atoms, in particular <$C_{10}$ and more preferably <$C_5$, such as methanol, ethanol, propanol.

Table 1 provided herein below lists some compounds by way of example.

Compounds of the formula II suitable for the process according to the present invention include, in particular, alkanols, preferably methanol ethanol, propanol, isopropanol, octanol, dodecanol, hexadecanol, octadecanol, and 2-ethylhexanol, and also polyols, in particular, ethylene glycol, diethylene glycol, polyethers, glycerol and trimethylolpropane. It is also possible to use amino alcohols such as ethanolamine, diethanolamine and triethanolamine, and also aromatic alcohols, in particular, phenol, benzyl alcohol and catechol, and alicyclic alcohols, in particular, cyclopentanol and cyclohexanol, but also unsaturated alcohols such as hexenol, hexadecenol and octadecenol. It is also possible in the context of the present invention to use suitable alcohols in mixtures with one another.

TABLE 1

Critical data of selected reaction alcohols:

| Alcohols | $T_k$/K | $p_k$/bar |
|---|---|---|
| Methanol | 512.6 | 80.9 |
| Ethanol | 513.9 | 61.4 |
| n-Propanol | 536.8 | 51.7 |
| 2-Propanol | 508.4 | 47.6 |
| Butanol | 563.0 | 44.2 |
| Octanol | 625.5 | 28.6 |
| Hexadecanol | 770.0 | 16.1 |
| Octadecanol | 790.0 | 12.8 |
| Glycercol | 726.05 | 66.9 |

$T_k$ = critical temperature in Kelvin, K.
$p_k$ = critical pressure in bars

The inventive reaction may optionally be carried out in the presence of suitable homogeneous and heterogeneous catalysts selected from the group of protic acids, in particular, HCl, $H_2SO_4$, $H_3PO_4$, acetic acid, citric acid, or of the salts, in particular, $AlCl_3$, $LiClO_4$, LiCl, $ZnCl_2$, $BiCl_3$, $Ti(OiPr)_4$ (OiPr=isopropoxide), rare earth heptafluorodimethyloctanedionates (=fod) and trifluoromethanesulfonates (=OTf), in particular, $Yb(fod)_3$, $Eu(fod)_3$, $Sc(OTf)_3$, $Yb(OTf)_3$, or the ion exchangers, in particular, Amberlyst-15, or the buffers, in particular $Na_3PO_4/H_3PO_4$. The direct reaction is effected preferably using highly concentrated suspensions of (poly) amino acids, proteins or peptides in alcohols, preferably without addition of activators or homogeneous catalysts.

The apparatuses used, or also used, in accordance with the present invention are suitable vessels having a stirrer for initial charge of the reaction partners, and also a pump for compressing the compound of the general formula II to or above the critical pressure. A suitable pump with suspension ball valves is sold, for example, by LEWA. In order to ensure a reaction, both the critical temperature and the critical pressure of the alcohol have to be exceeded. In order to obtain a sufficient reaction rate, the two parameters mentioned in Table 1 are preferably exceeded by from 5 to 15%. Table 1 lists some examples of critical parameters of alcohols. The reaction proceeds in a heatable reactor which can be operated continuously or batchwise.

The apparatus used in accordance with the invention is illustrated schematically in FIG. 1. The reactants are initially charged in a suitable stirred vessel (A). From this reservoir, the mixture is conveyed by a suitable pump (B) into the reactor (C). The pump is capable of bringing the mixture to a pressure at or above the critical pressure of the alcohol of the formula (II) in A. The heater (D) heats the reactor (C) to a temperature greater than or equal to the critical temperature of the alcohol. At the outlet of the reactor (C), a valve (E) can be used to control the pressure in the reaction setup. In addition, the residence times can thus be adjusted individually to the particular amino acid or the amino acid/peptide mixture, which allows the degradation of sensitive amino acids, for example, tyrsine or tryptophan, to be minimized. To minimize by-products, a carrier stream of pure ethanol from the reservoir (F) can be heated using the preheater (G) by means of the pump $B^1$. At the mixing point (H), the carrier stream (CS) is then mixed with the reactant stream (RS) and fed to the reactor. The ratio of CS/RS may lie within wide ranges including from 0/100 to 99/1, preferably from 20/80 to 80/20. When the preheating temperature selected is so high that there is already reaction temperature at the mixing point, the temperature gradient in the reactor is sufficiently small to prevent carbonization.

The product mixtures, which comprise the amino acid esters formed, may be introduced into an aqueous protic acid-containing solution. Thus, the acid addition salts of the amino acid esters are formed and have a distinctly increased stability in comparison to the free amino acid esters.

One or more protic acids may also be used, in particular, those selected from the group of formic acid, acetic acid, propionic acid, heptanoic acid, caprylic acid, nonanoic acid, capric acid, undecanoic acid, lauric acid, myristic acid, palmitic acid, stearic acid, arachic acid, behenic acid, cyclopentanecarboxylic acid, cyclohexanecarboxylic acid, acrylic acid, methacrylic acid, vinylacetic acid, crotonic acid, 2-/3-/4-pentenoic acid, 2-/3-/4-/5-hexenoic acid, lauroleic acid, myristoleic acid, palmitoleic acid, oleic acid, gadoleic acid, sorbic acid, linoleic acid, linolenic acid, pivalic acid, ethoxyacetic acid, phenylacetic acid, lactic acid, 2-ethylhexanoic acid, oxalic acid, glycolic acid, malic acid, malonic acid, succinic acid, tartaric acid, glutaric acid, citric acid, adipic acid, pimelic acid, suberic acid, azelaic acid, sebacic acid, benzoic acid, o-/m-/p-toluic acid, salicylic acid, 3-/4-hydroxybenzoic acid, phthalic acids, or the fully or partly hydrogenated derivatives thereof such as, for example, hexahydro- or tetrahydrophthalic acid, phosphoric acid, hydrochloric acid, sulfuric acid and mixtures thereof in particular, lactic acid, tartaric acid, acetic acid and hydrochloric acid.

For the identification of the reaction products, the product solutions are fed to suitable analytical methods. Especially GC, GC-MS, HPLC and MALDI have been found to be useful.

The following examples are provided to illustrate the process of the present invention. In the examples, analysis was carried out immediately after the experiments with HPLC and NMR All examples were carried out in an apparatus according to FIG. 1. For the conveying of the reaction mixtures, pumps of the LEWA TYP EK08 type with an HK 8 mm pump head were used.

USE EXAMPLE 1

Preparation of Diethyl Glutamate and Ethyl Pyroglutamate:

A mixture of ethanol and glutamic acid was initially charged in a stirred vessel (A). The fraction of glutamic acid was 0.1% of the ethanol fraction. The mixture was conveyed continuously through the reactor (C) at a pressure of 72 bar by a suitable pump (B). The tubular reactor (C) was heated to a temperature of 260° C. by the heater (D). A carrier stream of pure ethanol from the reservoir (F) was heated to the same temperature using the preheater (G). At the mixing point (H), the carrier stream was mixed with the reactant stream (ratio 50/50) and fed to the reactor (C). The preheating temperature selected was so high that there was already reaction temperature at the mixing point, so that the temperature gradient in the reactor (C) was sufficiently small to prevent carbonization at the wall. The residence time in the tubular reactor (C) was 40 sec. With the aid of the control valve (E), the pressure was kept at the target value mentioned. At the outlet of the system, the reacted solution was introduced into 1 molar HCl. According to HPLC, 50% product yield (ethyl pyroglutamate) was obtained.

USE EXAMPLE 2

Preparation of Ethyl Glycinate:

A mixture of ethanol and glycylglycine (GlyGly) was initially charged as a suspension in (A). The proportion of solids in the suspension was about 5%. This mixture was treated analogously to use example 1 and conveyed through the reactor. The mixture was conveyed continuously through the reactor (C) by a suitable pump (B) at a pressure of 90 bar. The tubular reactor (C) was heated to a temperature of 260° C. by the heater (D). A carrier stream of pure ethanol from the reservoir (F) was heated at the same temperature using the preheater (G). At the mixing point (H), the carrier stream was mixed with the reactant stream (50/50 ratio) and fed to the reactor (C). The preheating temperature selected was so high that there was already reaction temperature at the mixing point, so that the temperature gradient in the reactor was sufficiently small to prevent carbonization at the wall. The residence time of the reaction mixture in the reactor (C) was 40 sec. With the aid of the control valve (E), the pressure was kept at the target value mentioned. At the outlet of the system, the reaction mixture was introduced into 1 M HCl and fed to the analysis. HPLC identified ethyl glycylglycinate as a simple esterification product and ethyl glycinate as an esterification and cleavage product. The content of ester in the product make at the reactor outlet was on average approx. 1.5%. The yield was accordingly about 30%.

USE EXAMPLE 3

Ethanolysis of Caprolactam:

A mixture of ethanol and caprolactam was initially charged as a solution in (A). The fraction of caprolactam in the suspension was about 20% (w/w). This mixture was treated analogously to use example 1 and conveyed through the reactor (C). The mixture was conveyed continuously through the reactor (C) at a pressure of 72 bar by a suitable pump. The tubular reactor (C) was heated to a temperature of 350° C. by the heater (D). A carrier stream of pure ethanol from the reservoir (F) was heated to the same temperature using the preheater (G). At the mixing point (H), the carrier stream was mixed with the reactant stream (50/50 ratio) and fed to the reactor (C). The preheating temperature selected was so high that there was already reaction temperature at the mixing point, so that the temperature gradient in the reactor (C) was sufficiently low to prevent carbonization at the wall. The residence time in the tubular reactor (C) was 150 sec. With the aid of the control valve (E), the pressure was kept at the target value mentioned. At the outlet of the system, the reaction mixture was introduced into 1 M HCl and fed to the analysis. NMR spectroscopy identifies both 6-aminohexanoic acid as a cleavage product and ethyl 6-aminohexylcarboxylate as an esterification and cleavage product.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A process for preparing amino acid and peptide esters and/or acid addition salts thereof comprising reacting a least one monomeric or polymeric amino acid, peptide, or protein with an alcohol, wherein said reacting is performed in the presence of at least one supercritical alcohol.

2. The process as claimed in claim 1, wherein the reacting is carried out at a supercritical pressure and a supercritical temperature.

3. The process as claimed in claim 2, wherein the supercritical pressure and the supercritical temperature are at least 5% above a critical parameter of the alcohol.

4. The process as claimed in claim 1, wherein the reacting is carried out continuously or batchwise, and the reaction mixture has a residence time in a reactor of from 1 s to 24 h.

5. The continuous process as claimed in claim 1, wherein a carrier stream of the alcohol, preheated to a temperature of from 100° C. to 800° C. is added to a reactant stream upstream of a reactor inlet.

6. The process as claimed in claim 1, wherein the amino acid, peptide, protein or polyamide reacted is at least one of the compounds of general formula (I)

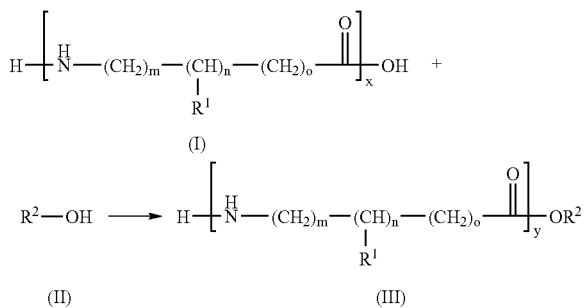

in which
- $R^1$ is at least one radical selected from the group of H, linear or branched aliphatic, alicyclic, heterocyclic, saturated, unsaturated or aromatic radical of proteinogenic or nonproteinogenic amino acids,
- n is at least 1,
- m,o are each independently from 0 to 20,
- x is $\geq 1$, and
- y is $\leq x$, preferably from 1 to 10,
- with at least one alcohol of the general formula (II),
in which
- $R^2$ is an optionally branched hydrocarbon radical optionally containing double bonds, hydroxyalkyl, alkyloxy, having from 1 to 30 carbon atoms, where the radical may also have alicyclic or heterocyclic components, saturated, unsaturated or aromatic, having a ring size of from 3 to 10 atoms, which may bear further, saturated or unsaturated hydrocarbon substituents having from 1 to 30 carbon atoms.

7. The process as claimed in claim 1, wherein the amino acids used are proteinogenic and nonproteinogenic amino acids.

8. The process as claimed in claim 7 wherein said proteinogenic and nonproteinogenic amino acids comprise glycine, lysine, aspartic acid, asparagine, alanine, proline, valine, glutamic acid, glutamine, leucine, isoleucine, serine, phenylalanine, tyrosine, histidine, threonine, cysteine, methionine, tryptophan, β-alanine, γ-aminobutyric acid, ω-aminocaproic acid, phenylglycine, arginine, amino acid derivatives, and also low and high molecular weight proteins.

9. The process as claimed in claim 8 wherein said proteins comprise casein, keratin, soya, collagen, wheat proteins, almond proteins, silk proteins, hydrolyzates thereof, poly(6-aminocaproic acid) and poly(12-aminododecanoic acid).

10. The process as claimed in claim 1, wherein said at least one alcohol comprises methanol, ethanol, propanol, isopropanol, butanol, hexanol, octanol, decanol, dodecanol, hexadecanol, octadecanol, glycol, glycerol, or propanediol.

11. The process as claimed in claim 1, wherein the reacting is carried out in the presence of suitable homogeneous and heterogeneous catalysts selected from the group of protic acids, rare earth heptafluorodimethyloctanedionates (=fod), rare earth trifluoromethanesulfonates (=OTf), ion exchangers, and buffers.

12. The process as claimed in claim 11 wherein said catalyst comprises one of HCl, $H_2SO_4$, $H_3PO_4$, acetic acid, citric acid, $AlCl_3$, $LiClO_4$, LiCl, $ZnCl_2$, $BiCl_3$, $Ti(OiPr)_4$, $Yb(fod)_3$, $Eu(fod)_3$, $Sc(OTf)_3$, $Yb(OTf)_3$, Amberlyst-15, or $Na_3PO_4/H_3PO_4$.

13. The process as claimed in claim 1 wherein acid addition salts of protic acids are produced.

14. The process as claimed in claim 13 further comprising as a reactant at least one acid.

15. The process as claimed in claim 14 wherein said at least one acid is selected from the group consisting of formic acid, acetic acid, propionic acid, heptanoic acid, caprylic acid, nonanoic acid, capric acid, undecanoic acid, lauric acid, myristic acid, palmitic acid, stearic acid, arachic acid, behenic acid, cyclopentanecarboxylic acid, cyclohexanecarboxylic acid, acrylic acid, methacrylic acid, vinylacetic acid, crotonic acid, 2-/3-/4-pentenoic acid, 2-/3-/4-/5-hexenoic acid, lauroleic acid, myristoleic acid, palmitoleic acid, oleic acid, gadoleic acid, sorbic acid, linoleic acid, linolenic acid, pivalic acid, ethoxyacetic acid, phenylacetic acid, lactic acid, 2-ethylhexanoic acid, oxalic acid, glycolic acid, malic acid, malonic acid, succinic acid, tartaric acid, glutaric acid, citric acid, adipic acid, pimelic acid, suberic acid, azelaic acid, sebacic acid, benzoic acid, o-/m-/p-toluic acid, salicylic acid, 3-/4-hydroxybenzoic acid, phthalic acids, or the fully or partly hydrogenated derivatives thereof such as hexahydro- or tetrahydrophthalic acid, phosphoric acid, hydrochloric acid, sulfuric acid and mixtures thereof.

* * * * *